United States Patent [19]

Orth et al.

[11] Patent Number: 4,582,910

[45] Date of Patent: Apr. 15, 1986

[54] METHOD FOR PREPARATION OF 4-HALOGENONAPHTHALIC ACID ANHYDRIDES

[75] Inventors: Winfried Orth, Hassloch; Emmerich Pastorek, Hemsbach; Werner Fickert, Mannheim, all of Fed. Rep. of Germany

[73] Assignee: Rütgerswerke Aktiengesellschaft, Frankfurt, Fed. Rep. of Germany

[21] Appl. No.: 703,006

[22] Filed: Feb. 19, 1985

[30] Foreign Application Priority Data

Mar. 27, 1984 [DE]  Fed. Rep. of Germany ....... 3411196

[51] Int. Cl.$^4$ .......................................... C07D 311/78
[52] U.S. Cl. .................................................. 549/232
[58] Field of Search ........................................ 549/232

[56] References Cited

U.S. PATENT DOCUMENTS

| | | | |
|---|---|---|---|
| 3,888,885 | 6/1975 | Deucker et al. | 549/232 |
| 3,954,810 | 5/1976 | Deucker et al. | 549/232 |
| 4,033,986 | 7/1977 | Castenson et al. | 549/232 |

OTHER PUBLICATIONS

Kamiya et al., Chemical Abstracts, vol. 83 (1975) 114076y.
Wakisaka et al., Chemical Abstracts, vol. 88 (1978) 120868c.

Primary Examiner—Richard L. Raymond
Attorney, Agent, or Firm—Beveridge, DeGrandi & Weilacher

[57] ABSTRACT

A method for the preparation of 4-halogenonaphthalic acid anhydrides by halogenation of an aqueous solution of an alkali salt of the naphthalic acid with halogen or alkali metal hypohalogenite wherein a solution of the alkali metal salt of the naphthalic acid is treated with a water soluble magnesium salt and at least an equal molar amount of an alkakli metal hydroxide, halogenating this reaction mixture at a temperature in the range of 10° to 25° C. and subsequently acidifying the reaction mixture. In a second embodiment of the invention, an aqueous solution of alkali metal carbonate is used in place of the magnesium salt and alkali metal hydroxide.

22 Claims, No Drawings

METHOD FOR PREPARATION OF 4-HALOGENONAPHTHALIC ACID ANHYDRIDES

The invention relates to a new simplified method for the preparation of a naphthalic acid anhydride substituted in the 4th position by a halogen atom. These compounds are valuable intermediate products for the preparation of dyestuffs and optical brightening agents.

The most simple and with regard to commercialization, also in respect of the raw material, the most economical method of synthesis resides in a direct halogenation.

The relatively large number of previously described prior art methods show that by selection of the reaction conditions and in particular the choice of the pH conditions of the reaction solution, a definite influence may be exerted on the outcome of the reaction and, accordingly, on the yield and purity of the end products.

This is described by Rule and Thomson in the Journal of the Chemical Society, 1937, p. 1764–67; to wit, that the bromination of naphthalic acid anhydride in an acid medium to 3-bromonaphthalic acid anhydride and in an alkaline medium to 4-bromonaphthalic acid anhydride can be carried out. However, in the alkaline medium because the alkali salt of the naphthalic acid is formed a yield of 4-bromonaphthalic acid anhydride of only 43% in mediocre purity is obtained. Through the use of more stringent reactor conditions, there will be produced tribromonaphthalic acid anhydride.

According to DE-PS No. 22 42 513 and DE-OS No. 2 302 372, the optimum reaction conditions for the chlorination as well as for the bromination of naphthalic acid anhydride (and the alkali salt of the naphthalic acid) are reaction temperatures in the range from 0° to 30° C. and a pH value of the reaction medium in the range of 6.8 to 9.0, preferably in the range of 7.2 to 7.8.

Also, according to the Japanese application No. 77 151 152 (C.A. 88, 120 868c) the formation of 4-chloronaphthalic acid anhydride by chlorination is described at a pH in the range of 6.8 to 9.0, however, at different temperatures.

Because of the fact that during the reaction a pH shift takes place, the regulation of the pH in such a narrow range through a running controlled neutralization during the reaction is very costly.

The disadvantage is overcome according to the method described in the Japanese application No. 75 58 042 (C.A. 83, 114076g). In accordance therewith with the procedure described therein, the chlorination of the alkali naphthalate is carried out in alkalihydroxide solution. However, with that an approximately 20% lower yield of 4-chloronaphthlic acid anhydride is obtained and the portion of the produced dichloronaphthalic acid anhydride is relatively high. In addition, several experiments have shown that with this conversion, a considerable amount (4%) of the undesired 3-chloronaphthalic acid anhydride is obtained.

It is therefore the object of the invention to provide a method for the preparation of 4-halogenonaphthalic acid anhydride which enables these products to be obtained by a simple halogenation without costly control of a narrow pH range, in good yields and in the highest possible purity.

The objects of the invention are achieved in accordance with the method for the preparation of 4-halogenonaphthalic acid anhydride through halogenation of an aqueous solution of an alkali metal salt of the naphthalic acid with halogen or alkali metal hypohalogenite wherein the solution of the alkali metal salt of the naphthalic acid is contacted with a water soluble magnesium salt and at least an equimolar amount of an alkali metal hydroxide and the reaction mixture is then halogenated at a temperature in the range of 10° to 25° and subsequently acidified. In a further embodiment, the process is carried out by utilizing an aqueous solution of alkali metal carbonate in place of the magnesium salt and alkali metal hydroxide and the formed solution is then halogenated at a temperature in the range of 10° to 25° and subsequently acidified. Still further, the object of the invention is achieved by carrying out the halogenation under intensive mixing in the presence of a water insoluble solvent material, such as an organic solvent, which is inert with respect to halogen. Most particularly, 4-bromonaphthalic acid anhydride can be obtained by utilizing bromochloride as the bromination material.

In spite of the fact that with this method, the pH value of the reaction mixture during the halogenation reaction is in the range of 9.3 to 13 depending upon the amounts of the alkali, it has surprisingly been found that the 4-halogenonaphthalic acid anhydride product is obtained in high yield and purity. The halogenation is carried out in a simple manner through introduction of molecular halogen or through the addition of a hypohalogenite; e.g. sodium or potassium hypochlorite, without further control or regulation of the pH value of the reaction solution. A preferable bromination material is the composition known as bromochloride which contains both the halogens, chlorine and bromine, together.

An additional increase of the reaction velocity, yield, and purity is obtained when the halogenation is carried out under intensive mixing in the presence of a water insoluble solvent material which is inert towards halogen.

It is conceivable that with the help of a suitable solvent, the apportionment of the halogens, and with that the halogenation reaction can be simplified. It is surprising that according to the invention, the production of undesirable dihalogen derivatives is not increased but instead is slightly lowered. A further unforeseen advantage in the use of such a solvent resides in the fact that the 4-halogenonaphthalic acid anhydride compounds, which are usually filterable only with difficulty, can now be obtained in accordance with the variations of the methods described in the present invention in a form which is easily filterable.

Starting products suitable for carrying out the method of the invention are naphthalic acid anhydride, as a pure substance, or in the form of a technical grade quality. The naphthalic acid anhydride together with an equivalent amount of alkali metal hydroxide, preferably potassium hydroxide, in water, is advantageously mixed in a warmed condition and proceeds into solution as the alkali metal salt of the naphthalic acid (alkalinaphthalate).

This solution is then cooled to 10° to 25° C. and is converted with a water soluble magnesium salt and alkali hydroxide. As a result, the magnesium hydroxide precipitates out in very finely divided form. As the magnesium salt, there may be considered all water soluble salts or salt mixtures. For commercial reasons, the most advantageously utilized magnesium salts are magnesium chloride or sulfate. Although with the conversion with alkali hydroxide, insoluble magnesium hydroxide is obtained, it is not advisable to directly introduce a solid powdery magnesium hydroxide. There should be introduced, as a minimum, the amount equal to the molar quantity of the naphthalic acid anhydride, preferably an excess of 10% to 50% can be used. However, a greater excess amount does not interfere with the reaction when considered from the standpoint of commercial development. The magnesium salt can be used as the solid salt or advantageously may be dissolved in water. The amount of the alkali salt solution to be used should be equivalent at least to the amount of magnesium salt. Advantageously, it is also to be encouraged to use an excess of from 10 to 20%. According to the amount of alkali hydroxide used, one will obtain a pH value of the reaction mixture in the range of 11 to 13.

In a second embodiment of the invention, there is employed as the reaction solution, a solution of the alkali salt of the naphthalic acid which contains alkali carbonate. This reaction solution can be prepared either by forming an alkali naphthate solution from naphthalic acid anhydride and alkali metal hydroxide solutions, which is treated with alkali carbonate or by dissolving naphthalic acid anhydride in the amount of 2.1 to 5.5 times the molar amount of an aqueous alkali carbonate solution. According to the amount of alkali carbonate used, the pH value of the solution will lie in the range of 9.5 to 12.5.

In accordance with a variation of the invention, halogen or halogenite is introduced into the prepared reaction solution at a temperature in the range of 10° to 25° C., or halogen is introduced over the solution, wherein the amount of halogen is preferably less than double the molar amount of the naphthalic acid anhydride that is used. After the addition of the halogen, the reaction mixture is stirred for another 1 to 3 hours, wherein optionally the reaction temperature may be raised up to about 50° C. After that, the mixture is acidified with a strong acid and the precipitated product can be separated in a known manner and purified.

A further improvement in the preparation of the present invention resides in converting the reaction solution or mixture with approximately 5 to 15 volume percent of a water insoluble solvent and which under the reaction parameters is inert to halogen and carrying out intensive mixing of the halogenation reaction. Advantageously, such solvents are lower halogenalkanes or halogenaryls such as for example methylenechloride, tetrachloromethane, ethylenechloride, trichloroethane, trichloropropane or chlorobenzol. After the completion of the conversion, these solvents can be recovered through distillation and can be utilized again in further reaction procedures.

The following examples serve to illustrate the present invention but are not limiting thereof in any respect.

EXAMPLE 1

297 g (1.5 mol) naphthalic acid anhydride are dissolved in 4500 ml water and 240 g (3 mol) 50% caustic soda solution with stirring at 80° C. To the solution which is cooled to 20° to 25° C., there is added all at one time a solution which is prepared from 813 g (3.3 mol) magnesium sulfate .7H$_2$O and 1200 ml water. Immediately thereafter, 288 g (3.6 mol) of a 50% caustic soda solution are slowly added dropwise and as a result, the magnesium hydroxide precipitates out. To this suspension, there is then added 200 ml ethylenechloride and then within 4½ hours and at a temperature of 20° to 25° C., 190 g (2.8 mol) chlorine is introduced over the surface of the reaction mixture. Thereafter, one stirs for an additional 1 hour. Following the after reaction, the reaction mixture is carefully brought to a pH of 1 to 0.5 by the addition of about 370 ml (4.4 mol) concentrated hydrochloric acid and the ethylenechloride is distilled off. The precipitated product is then recovered by siphoning off at about 40° C. and is washed free of sulfate and is then dried at 60° to 110° C. The yield is 302 g which is equal to 86.8% of the theoretical yield. The purity (gas chromatographic analysis) is 94 to 95%.

EXAMPLE 2

900 g (6.5 mol) potassium carbonate is dissolved by stirring in 4500 ml water is converted in portions at 80° C. with 594 g (3 mol) naphthalic acid anhydride and is then stirred to complete dissolution. After cooling of this solution to 20° C. and the addition of 480 ml trichloromethane, 339 g (4.8 mol) chlorine are then introduced over the reaction mixture at 20° to 25° C. over a period of 4½ hours. Out of the reaction mixture, there is vaporized during the chlorination a continuous stream of carbon dioxide which also conveys with it a small portion of the chlorine. Subsequently, the reaction mixture is stirred for 1 to 2 hours at 20° to 25° C. until no further reaction can be detected on a potassium iodide starch paper. The lower trichloromethane layer (containing side products) is separated off and an additional 300 ml of fresh trichloromethane is introduced. After the subsequent reaction, the reaction mixture is carefully with 645 ml (7.6 mol) concentrated hydrochloric acid brought to a pH of 0.5 and the trichloromethane is then distilled off. The utilization of the organic solvent material accomplishes, in addition to an increased conversion velocity rate, an increase in the yield and purity, and even better filterability and a lower water content of the wet product. Without utilization of trichloromethane, the water content ranges up to 80% and with this procedure approximately only 50%. At approximately 40° C., the product is removed by siphoning off, is washed free of chloride and dried at 60° to 110° C.

Yield: 600 g—86.0% of theory.

Content (gas chromatography): 94%.

EXAMPLE 3

4-chloronaphthalic acid anhydride is prepared analogously to Example 1, however without utilization of ethylene chloride. After carrying through with the reaction sequences as described, the following characteristics are obtained:

Yield: 288 g=82.8% of theory.

Content (gas chromatography): 91%.

EXAMPLE 4

198 g (1 mol) naphthalic acid anhydride is dissolved by stirring in 3000 ml water and 276 g (2 mol) potassium carbonate at 80° C. The solution is cooled to 20° to 25° C. and over the course of 2 hours, 979 g (1.6 mol) 12% sodium hypochlorite solution is added and is stirred for 5 hours at 20° to 25° C. The reaction mixture is brought to a pH of 1 with the addition of hydrochloric acid, is siphoned off and the filter residue is washed free of chloride and is dried at 60° to 110° C.

Yield: 190 g 4-chloronaphthalic acid anhydride=81.7% of theory.

Purity (gas chromatography): 90%.

EXAMPLE 5

300 g (2.17 mol) potassium carbonate are dissolved with stirring in 1000 ml water. To that there is added in portions at 80° C., 198 g (1 mol) naphthalic acid anhydride and is stirred at 80° C. until complete dissolution. After cooling to 20° C., there is added over the course of 4 hours, a bromine solution which is formed from 280 g (1.3 mol) bromine and 200 ml ethylene chloride. This is stirred for an additional 1 hour at 18° to 22° C. With longer after reaction times or with standing, the reaction mixture darkens. The reaction mixture is then brought to a pH of 1 through the simultaneous addition of 800 ml of 10% hydrochloric acid with stirring and after that is stirred for an additional 15 to 20 minutes. The product then precipitates and is filtered in accordance with conventional means and is dried.

Yield: 230 g 4-bromonaphthalic acid anhydride = 83% of theory.

Content: (gas chromatography): 88%.

EXAMPLE 6

300 g (2.17 mol) potassium carbonate are dissolved in 1500 ml water with stirring, and then in portions is converted with 198 g (1 mol) naphthalic acid anhydride at 80° C. and stirred until complete dissolution is obtained. After cooling of this solution to 20° C., a solution of 196 g (1.7 mol) bromochloride in 180 ml tetrachloromethane is introduced dropwise into the reaction mixture at 20° C. within the course of about 4½ hours. Subsequently, the reaction mixture is stirred for 2 hours at 20° to 25° C. The reaction product is treated as described in Example 1.

Yield: 218 g 4-bromonaphthalic acid anhydride = 78.7% of theory.

Content: (gas chromatography): 91%.

While chlorine, bromine and bromochloride are specifically referred to as halogenating substances, other halogens may also be used. Further, while sodium and potassium are referred to as the preferred alkali metals, it should be understood that other alkali metals, as well, are contemplated whenever the term appears.

Further variations and modifications of the present invention will become apparent to those skilled in the art from the foregoing description of the invention which are intended to be encompassed by the claims appended hereto.

We claim:

1. A method for the preparation of 4-halogenonaphthalic acid anhydride comprising mixing a solution of an alkali metal salt of naphthalic acid with a water soluble magnesium salt and at least an equimolar amount of an alkali metal hydroxide to form a reaction mixture, halogenating said reaction mixture with halogen or alkali metal hypohalogenite at a temperature in the range of 10° to 25° C. to form a halogenated reaction mixture, and then treating the halogenated reaction mixture with an acid and recovering the desired product.

2. The method according to claim 1, wherein the reaction is carried out under intensive mixing in the presence of an inert solvent which is water insoluble and unreactive with halogen under the conditions of the reaction.

3. The method according to claim 1, wherein the bromochloride is used for said halogenating.

4. The method according to claim 1, wherein the magnesium salt is magnesium chloride or magnesium sulfate.

5. The method according to claim 1, wherein the magnesium salt is used as a solid salt.

6. The method according to claim 1, wherein the magnesium salt is used as an aqueous solution of the salt.

7. The method according to claim 1, further comprising initially forming a solution of an alkali metal salt of the naphthalic acid by mixing naphthalic acid anhydride with alkali metal hydroxide in water.

8. The method according to claim 1, wherein the halogen or alkali metal hypohalogenite is used in an amount less than double the molar amount of the naphthalic acid anhydride that is used, and wherein the reaction mixture is stirred 1 to 3 hours after the halogenating is carried out, and the temperature is increased to a temperature in the range up to about 50° C.

9. The method according to claim 8, wherein the reaction is carried out under intensive mixing in the presence of an inert solvent which is water insoluble and unreactive with halogen under the conditions of the reaction.

10. The method according to claim 9, wherein bromochloride is used in the halogenating.

11. A method for the preparation of 4-halogenonaphthalic acid anhydride comprising mixing a solution of an alkali metal salt of naphthalic acid with alkali metal carbonate to form a reaction mixture having a pH in the range of 9.3 to 13 and halogenating said reaction mixture with halogen or alkali metal hypohalogenite, at a temperature in the range of 10° to 25° C. to form a halogenated reaction mixture and then treating the halogenated reaction mixture with an acid and recovering the desired product.

12. The method according to claim 11, wherein the reaction is carried out under intensive mixing in the presence of an inert solvent which is water insoluble and unreactive with halogen under the conditions of the reaction.

13. The method according to claim 11, wherein the bromochloride is used for halogenating.

14. The method according to claim 11, further comprising initially forming a solution of an alkali metal salt of naphthalic acid by dissolving naphthalic acid anhydride in 2.1 to 5.5 times the molar amount of an aqueous alkali metal carbonate solution.

15. The method according to claim 14, further comprising wherein the reaction is carried out under intensive mixing in the presence of an inert solvent which is water insoluble and unreactive with halogen under the conditions of the reaction.

16. The method according to claim 14, wherein bromochloride is used for halogenating.

17. The method according to claim 11, further comprising initially forming a solution of an alkali metal salt of the naphthalic acid by mixing naphthalic acid anhydride with alkali metal hydroxide and treating the solution with alkali metal carbonate.

18. The method according to claim 17, further comprising wherein the reaction is carried out under intensive mixing in the presence of an inert solvent which is water insoluble and unreactive with halogen under the conditions of the reaction.

19. The method according to claim 18, wherein bromochloride is used for halogenating.

20. The method according to claim 11, wherein the halogen or alkali metal hypohalogenite is used in an amount less than double the molar amount of the naphthalic acid anhydride this is used, and wherein the reaction mixture is stirred 1 to 3 hours after the halogenating is carried out, and increasing the temperature to a temperature in the range of up to about 50° C.

21. The method according to claim 20, wherein the reaction is carried out under intensive mixing in the presence of an inert solvent which is water insoluble and unreactive with halogen under the conditions of the reaction.

22. The method according to claim 21, wherein bromochloride is used in the halogenating.

* * * * *